United States Patent [19]

Godek et al.

[11] Patent Number: 5,138,060
[45] Date of Patent: Aug. 11, 1992

[54] PROCESS AND INTERMEDIATES FOR PREPARING AZABICYCLO(2.2.2)OCTAN-3-IMINES

[75] Inventors: Dennis M. Godek, Glastonbury; Charles W. Murtiashaw, North Stonington, both of Conn.

[73] Assignee: Pfizer Inc., New York, N.Y.

[21] Appl. No.: 637,102

[22] Filed: Jan. 3, 1991

[51] Int. Cl.$^5$ ............................................. C07D 453/02
[52] U.S. Cl. ..................................................... 546/133
[58] Field of Search ......................... 546/133; 514/305

[56] References Cited

U.S. PATENT DOCUMENTS

| | | | |
|---|---|---|---|
| 3,993,652 | 11/1976 | Bechara et al. | 546/133 |
| 4,203,990 | 5/1980 | Yen | 546/133 |
| 4,657,911 | 4/1987 | Imbert et al. | 546/133 |

FOREIGN PATENT DOCUMENTS

90/05729  5/1990  World Int. Prop. O. .

*Primary Examiner*—C. Warren Ivy
*Assistant Examiner*—Catherine S. Kilby Scalzo
*Attorney, Agent, or Firm*—Peter C. Richardson; Paul H. Ginsburg; Gezina Holtrust

[57] ABSTRACT

Azabicyclo[2.2.2]octan-3-imines of the general formula

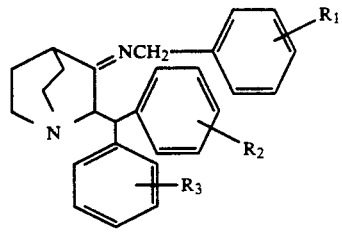

wherein $R_1$, $R_2$ and $R_3$ are as defined herein are prepared by reacting a compound of the formula

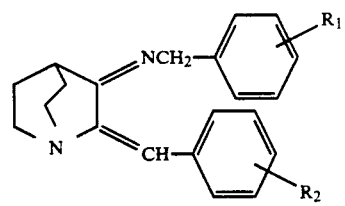

with a compound of the formula

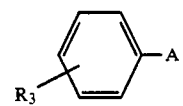

wherein A is MgCl, MgBr or Li.

3 Claims, No Drawings

PROCESS AND INTERMEDIATES FOR PREPARING AZABICYCLO(2.2.2)OCTAN-3-IMINES

BACKGROUND OF THE INVENTION

The present invention relates to processes and intermediates for the preparation of azabicyclo-[2.2.2]octan-3-imines which in turn are intermediates for the preparation of substituted 2-diphenylmethyl-N-phenylmethyl-1-azabicyclo[2.2.2]octan-3-amino compounds having Substance P antagonizing properties ("the final compounds"). The invention also relates to phenylmethylene imine intermediates for making the azabicyclo[2.2.2]octan-3-imines and to a process for making them. The invention further relates to a process for preparing the cis-compounds of the final compounds from the azabicyclo[2.2.2]octan-3-imines, and a process for resolving a racemic mixture of the cis-compound.

The final compounds, a process for their preparation, and their ability to antagonize Substance P are described in International Publication WO 90/05729. These compounds are of use in the treatment of diseases caused by an excess of Substance P. Substance P is a naturally occurring undecapeptide belonging to the tachykinin family of peptides, the latter being so-named because of their prompt stimulatory action on smooth muscle tissue. More specifically, substance P is a pharmacologically-active neuropeptide that is produced in mammals (having originally been isolated from gut) and possesses a characteristic amino acid sequence. The wide involvement of substance P and other tachykinins in the pathophysiology of numerous diseases has been amply demonstrated in the art. Examples of such diseases are psychosis, migraine, rheumatoid arthritis and ulcerative colitis.

SUMMARY OF THE INVENTION

The present invention relates to a process for preparing a compound of the formula

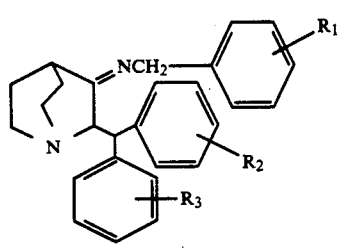

wherein $R_1$, $R_2$ and $R_3$ are independently hydrogen, or one or two substituents selected from the group consisting of fluorine, chlorine, bromine, trifluoromethyl, alkyl having from one to three carbon atoms and alkoxy having from one to three carbon atoms, by reacting a compound of the formula

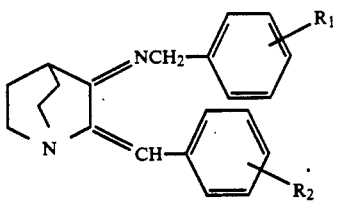

wherein $R_1$ and $R_2$ are as defined above, with a compound of the formula

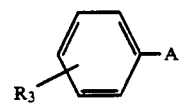

wherein $R_3$ is as defined above and A is MgCl, MgBr or lithium.

In a specific embodiment of the process, $R_1$ is orthosubstituted, e.g. o-methoxy or o-halo such as o-chloro, and $R_2$ and $R_3$ are each hydrogen. In other specific embodiments, $R_1$ is one of alkoxy, e.g., o-methoxy, and one of halo, e.g., 5-halo, or $R_1$ is two alkoxys, e.g., $R_1$ is 2,5-dimethoxy.

The invention also relates to a process for preparing a compound of the formula

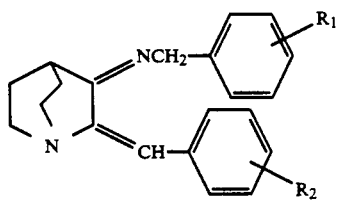

wherein $R_1$ and $R_2$ are independently hydrogen, or one or two substituents selected from the group consisting of fluorine, chlorine, bromine, trifluoromethyl, alkyl having from one to three carbon atoms or alkoxy having from one to three carbon atoms, by reacting a compound of the formula

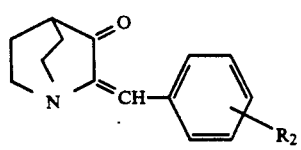

wherein $R_2$ is as defined above in connection with formula I, with a compound of the formula

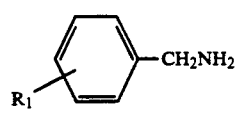

wherein $R_1$ is as defined above in connection with formula I. In a specific embodiment of the process, $R_1$ is orthosubstituted, e.g. o-methoxy or o-halo such as o-chloro, and $R_2$ and $R_3$ are each hydrogen.

The invention also relates to the overall process of preparing compounds of formula I by reacting the compounds of formulas II and III wherein the compounds of formula II are made by reacting the compounds of formulas IV and V. In a specific embodiment of such process, $R_1$ is orthosubstituted, e.g. o-methoxy or o-halo such as o-chloro, and $R_2$ and $R_3$ are each hydrogen. In other embodiments, $R_1$ is disubstituted by one alkoxy, e.g., o-methoxy, and one of halo, or $R_1$ is disubstituted by two alkoxys, e.g., $R_1$ is 2,5-dimethoxy.

The invention further relates to a process for preparing a racemic mixture of a cis-compound of the formula

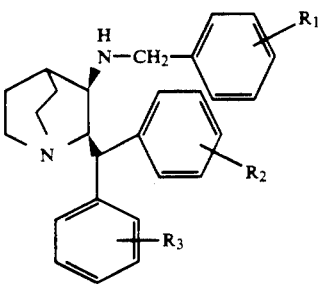

VI wherein $R_1$, $R_2$ and $R_3$ are independently hydrogen, or one or two substituents selected from the group consisting of fluorine, chlorine, bromine, trifluoromethyl, alkyl having from one to three carbon atoms or alkoxy having from one to three carbon atoms, by reducing a compound of the formula

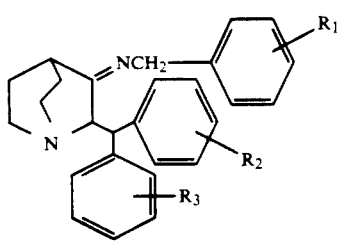

I with sodium triacetoxyborohydride and acetic acid. In a specific embodiment of this process, $R_1$ is orthosubstituted, e.g. o-methoxy or o-halo such as o-chloro, and $R_2$ and $R_3$ are each hydrogen. In another embodiment, $R_1$ is disubstituted by one alkoxy, e.g., o-methoxy and one halo, e.g., 5-halo, or $R_1$ is disubstituted by two alkoxys, e.g., $R_1$ is 2,5-dimethoxy.

The invention further relates to a process for resolving a racemic mixture of a cis-compound of the formula

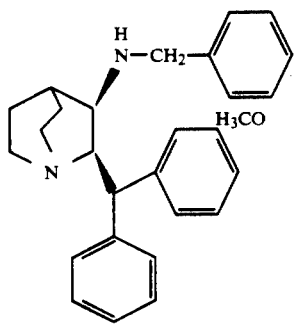

VII by reacting the racemic mixture with (−)mandelic acid, purifying the (−)mandelate salt of the compound of formula VI, treatment of the (−)mandelate salt with strong base, and recovering the (−) compound of formula VII.

The invention further relates to a compound of the formula

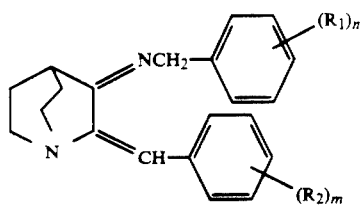

II wherein n and m are each independently 0, 1 or 2, and $R_1$ and $R_2$ are independently fluorine, chlorine, bromine, trifluoromethyl, alkyl having from one to three carbon atoms or alkoxy having from one to three carbon atoms.

In a specific embodiment of the compound, n is 1, $R_1$ is at the ortho position, e.g. O-methoxy, or O-halo such as O-chloro, and m is o. In another embodiment, n is 2, one $R_1$ is an alkoxy at the ortho position, e.g. O-methoxy, and one $R_1$ is halo, e.g. 5-halo, or n is 2, and $R_1$ is an alkoxy, e.g. $(R_1)_n$ is 2,5-dimethoxy.

DETAILED DESCRIPTION OF THE INVENTION

The reaction of a compound of formula II with a compound of formula III is performed in a reaction-inert solvent capable of dissolving the Grignard reagent of formula III. Suitable solvents are ethers such as di($C_1$–$C_6$)alkyl ethers or cyclic ethers, e.g. tetrahydrofuran or dioxane. Other suitable solvents are toluene, dimethoxy-ethane and glymes. Mixtures of these solvents may be used as well. The reaction temperatures generally range from about 0° C. to room temperature. Higher reaction temperatures of up to about 50° C. and higher may be used to increase reaction speed.

The reaction of a compound of formula IV with a compound of formula V is performed in a reaction-inert organic solvent such as aromatic hydrocarbon solvents, e.g. toluene, xylene or benzene. The reaction is generally conducted at temperatures ranging from room temperature to the reflux temperature of the reaction-inert solvent. Generally, an acid catalyst is present during the reaction. Examples of such catalysts are sulfonic acids such as camphor sulfonic acid and p-toluene sulfonic acid.

The reduction of a compound of the formula I with sodium triacetoxyborohydride and acetic acid is generally carried out at about 5° to about 50° C., usually at about 20° to about 25° C. such as at room temperature.

The reaction of a compound of the formula VII with (−) mandelic acid is generally carried out in ethyl acetate. The subsequent purification is generally done by slurrying of the (−)mandelate salt in ethyl acetate at reflux temperatures. The purified salt is treated with strong base to recover the (−) compound of formula VII. The treatment is generally at a pH of 10 to 12. Examples of strong bases are strong inorganic bases such as alkali metal hydroxides, e.g. sodium hydroxide, and alkali metal carbonates such as potassium carbonate.

The final compounds of this invention can be administered by either the oral, parenteral or topical routes, at dosages ranging from about 5.0 mg to about 1500 mg per day as explained in more detail in above mentioned International Publication WO 90/05729.

The activity of the final compounds of the present invention, as substance P antagonists, is determined by their ability to inhibit the binding of substance P at its receptor sites in bovine caudate tissue, employing radioactive ligands to visualize the tachykinin receptors by means of autoradiography. The substance P antagonist activity of the herein described quinuclidine compounds is evaluated by using the standard assay procedure described by M. A. Cascieri et at., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

The following Examples illustrate the invention.

EXAMPLE 1

A.
N-[(2-methoxyphenyl)methyl]-2-phenylmethylene-1-azabicyclo[2.2.2]octan-3-imine To a 12 L three neck round bottom flask (3nrbf) fitted with mechanical stirrer, thermometer, condenser, and Dean Stark trap, was charged 5.9 L toluene, 791.8 g (3.7 moles) of 2-phenylmethylene-1-azabicyclo[2.2.2]octan-3-one, 764 g (5.6 moles, 1.5 equivalents) 2-methoxybenzylamine, and 8.8 g (0.039 moles) (+)camphor sulfonic acid. The solution was heated to reflux (116° C.) and refluxed for 42 hours. A total of 75 ml water was collected in the Dean Stark trap showing that the reaction was proceeding. The solution containing the title product was cooled to room temperature.

On isolation, the following NMR data were obtained:
$^1$H NMR(CDCl$_3$): 8.05 (d, 2H), 7.40–6.80 (m,9H), 4.80 (s, 2H), 3.80 (s,3H), 3.25–2.95 (m, 5H), 1.90–1.70 (m, 4H).

B.
2-(Diphenylmethyl)-N-[(2-methoxyphenyl)methyl]-1-azabicyclo[2.2.2]octan-3-imine.

The solution obtained in part A of this Example was slowly charged to a 22 L 3nrbf containing 1.8 L (5.6 moles, 1.5 equivalents) 3M phenylmagnesium bromide/diethyl ether solution at 5° C. The toluene solution was added over a 1.5 hour period while maintaining the temperature at less than 10° C. A tan slurry resulted after about half of the toluene solution was added. The reaction was stirred for 12–8 hours while warming to room temperature. The tan slurry was cooled to 5° C., and slowly quenched with 6.1L water over a 1.5 hour period. A 500 g portion of Celite was added to the quenched reaction, which was warmed to 30° C. and stirred at 30° C. for 30 minutes. The slurry was filtered through Celite and washed with toluene. The layers were separated, the aqueous layer washed with 1 L toluene, and the organic layers were combined and dried with 500 g magnesium sulfate for 30 minutes. The slurry was filtered and the filtrate was vacuum evaporated to a thick oily solid. Isopropanol (4.5 L) was charged to the thick oily solid, the resulting slurry cooled to 5° C., and granulated at this temperature for one hour. The solids were filtered off, washed with 0.5L cold isopropanol and vacuum dried at 50° C. giving 464.9 g (30.5% over the two steps) of the title compound. Melting point: 154°–158° C. $^1$H NMR(CDCl$_3$): 7.45–6.70 (m, 14H), 4.65 (d, 1H), 4.45 (q, 2H), 4.25 (d, 2H), 3.80 (s, 3H), 3.15–3.00 (m, 3H), 2.70–2.35 (m, 2H), 1.85–1.65 (m, 4H).

EXAMPLE 2

2-Diphenylmethyl-N-[(2-methoxyphenyl)methyl]-1-azabicyclo[2.2.2]octan-3-amino

To a 22L 3nrbf was charged 10.3 L acetic acid, followed by 531.1 g (2.5 moles) sodium triacetoxyborohydride over a 15 minute period. To this solution was added 411.5 g (1.0 moles) of the title compound of Example 1B over a 20 minute period. The temperature rose from 25 to 30° C. during this addition. The reaction was stirred at ambient temperature for 4.5 hours, and then concentrated to a thick oil. The oil was partitioned between 3.1L methylene chloride and 6.3L water. The pH of this mixture was adjusted from 4.2 to 8.4 with 645 ml of 50% sodium hydroxide. The layers were separated, the aqueous layer was washed with 1.4L methylene chloride and the organic layers were combined and dried for 30 minutes with magnesium sulfate. The slurry was filtered and the filtrate vacuum evaporated to an oil. The oil was diluted with 3.3L isopropanol which resulted in the thick precipitation of white solids. The slurry was heated under vacuum to 35° C. to remove the remaining methylene chloride, cooled to 5° C. and granulated for 30 minutes. The white solids were isolated via filtration, washed with cold isopropanol, and vacuum dried at 45° C. giving 356 grams of title product (racemic mixture) in 86.1% yield. The melting point was 133°–135° C.

EXAMPLE 3

(−)-2-Diphenylmethyl-N-[(2-methoxyphenyl)methyl]-1-azabicyclo[2.2.2]octan-3-amino In a 22L 3nrbf fitted with a mechanical stirrer and thermometer, was charged 345 g (0.84 moles) of the title compound of Example 2 and 10.4L ethyl acetate. The reaction was stirred for 10 minutes at 25° C. which resulted in a hazy solution. To this solution was charged 127.2 g (0.84 moles) (−)-mandelic acid, which resulted in a white slurry after stirring about four minutes at 20°–25° C. The reaction mixture was stirred at this temperature for 2 hours, then the white solids were isolated by filtration, washed with ethyl acetate, and air dried giving 386 g (81.8%) of the mandelate salt. This yield represents a 31.8% excess of the desired diastereomeric salt for which the theoretical yield is 236 g.

The salt was purified with the following procedure. The impure mandelate salt (386 g) was slurried in 7.7L refluxing ethyl acetate for 45 minutes, cooled to 20°–25° C. over a 1.5 hour period, filtered, and washed with about 1L ethyl acetate. The solvent wet cake was slurried in 5.5L refluxing ethyl acetate for 45 minutes, cooled to 20°–25° C. over a 1 hour period, filtered, and washed with about 1L ethyl acetate. The solvent wet cake was slurried in 4.0L refluxing ethyl acetate for 45 minutes, cooled to 20°–25° C. over a 2 hour period, filtered, washed with about 1L ethyl acetate, and air dried giving 199.6 g (84.6% yield) of the desired diastereomeric salt. The specific rotation for this mandelate salt was $[\alpha]_D = -51.5°$ (CH$_2$Cl$_2$, c=0.55), and the melting point was 196°–198° C.

A 12L 3nrbf was fitted with a mechanical stirrer, thermometer, and a pH meter. To the flask was charged 198.6 g (0.35 moles) of the purified mandelate salt, 3.97L water, and 3.4L methylene chloride. The pH of the two phase mixture was 5.2, and was adjusted to pH 13-14 with 44 ml 50% sodium hydroxide. The temperature during the sodium hydroxide addition was 18° C. The layers were separated and the aqueous layer was washed with 1.7 L methylene chloride. The organic layers were combined, backwashed with 2L water, dried with magnesium sulfate, and filtered. The filtrate was concentrated atmospherically to about 0.5L, then displaced with about 0.5L isopropanol to a volume of 0.5 L and a temperature of 60° C. Another 0.5L isopropanol was added, and the reaction was allowed to cool to 20°-25° C. over a 1.5 hour period. During the cooling period, a white slurry developed which was isolated by filtration, washed with isopropanol, and vacuum dried giving 115.5 g (67.0% yield) of the title product, which is the desired enantiomer, from a possible 172.5 g from the 345 g racemic starting material. The specific rotation of this material was $[\alpha]_D = -22.2°$ (CH$_2$Cl$_2$, c=0.50), and the melting point was 155°-157° C.

EXAMPLE 4

To a 5 L 3nrbf fitted with mechanical stirrer, thermometer, addition funnel, and steam bath, was charged 123.3 g (0.30 moles) of the title product of Example 3 and 3.1L acetone. The slurry was heated to 30° C. for dissolution, then cooled back to 24° C. A solution of 58.6 g (0.60 moles) methane sulfonic acid dissolved in 252 ml acetone, was charged in a 5 minute period. The reaction warmed up from 24° C. to 32° C., and became a thick white slurry which was stirred at ambient temperature for 2 hours. The reaction was concentrated atmospherically to a slurry volume of 300-400 ml and a temperature of 60° C. To the slurry was charged 750 ml methanol which dissolved the solid material. The solution was made "speck free" by filtration, and concentrated atmospherically to a volume of 150-200 ml. A 500 ml portion of filtered isopropanol was charged, and the reaction was concentrated under vacuum to 150-200 ml. Another 500 ml filtered isopropanol was charged, and the reaction was vacuum concentrated to a final volume of 500 ml and a temperature of 45° C. As the reaction cooled, crystallization occurred. The slurry was stirred for 1.5 hours while cooling to ambient temperature, then stirred at 5° C. for 45 minutes. The product was isolated by filtration, and the cake was washed twice with 200 ml cold filtered isopropanol. After vacuum drying at 45° C. for 12 hours, 170.7 g (94.4%) of the methane sulfonic acid salt of the title product of Example 3 was obtained. The melting point was 244.5°-246° C., and the specific rotation was $[\alpha]_D = -25.8°$ (CH$_3$OH, c=1.1).

We claim:
1. A compound of the formula

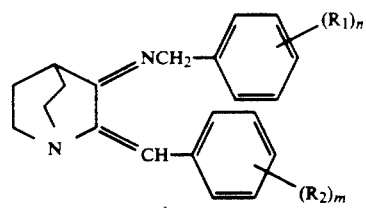

wherein n and m are each independently 0, 1 or 2, and R$_1$ and R$_2$ are independently fluorine, chlorine, bromine, trifluoromethyl, alkyl having from one to three carbon atoms or alkoxy having from one to three carbon atoms.

2. A compound according to claim 1 wherein n is 1, R$_1$ is at the ortho position, and m is 0.

3. A compound according to claim 1 wherein n is 1, R$_1$ is ortho-methoxy, and m is 0.

* * * * *